United States Patent [19]

Hildebrand

[11] 4,147,957
[45] Apr. 3, 1979

[54] PLASMA JET DEVICE AND METHOD OF OPERATING SAME

[75] Inventor: Karl J. Hildebrand, Tyngsboro, Mass.

[73] Assignee: SpectraMetrics, Incorporated, Andover, Mass.

[21] Appl. No.: 869,164

[22] Filed: Jan. 13, 1978

[51] Int. Cl.² .................. G01J 3/30; H01H 1/00; H05B 41/16
[52] U.S. Cl. ................ 315/111.2; 219/121 P; 313/231.4; 315/167; 356/316
[58] Field of Search ................ 313/231.4, 231.6; 315/111.2, 167; 356/85, 86; 219/121 P

[56] References Cited

U.S. PATENT DOCUMENTS

| 3,596,128 | 7/1971 | Elliott | 313/231.6 |
| 3,798,408 | 3/1974 | Foex et al. | 219/121 P |
| 3,989,512 | 11/1976 | Sayce | 219/121 P X |
| 4,009,413 | 2/1977 | Elliott et al. | 313/231.4 X |

Primary Examiner—Palmer C. Demeo
Attorney, Agent, or Firm—Richard P. Crowley

[57] ABSTRACT

A plasma jet device which comprises first and second anode electrodes spaced apart and positioned such that their axes, if extended, would intersect at an angle, and a third cathode electrode positioned offset from the plane formed by the extended axes of the first and second electrodes, the plasma jet device forming an ionized column of gas having the shape of an inverted Y and providing a stabilized excitation zone.

18 Claims, 1 Drawing Figure

PLASMA JET DEVICE AND METHOD OF OPERATING SAME

BACKGROUND OF THE INVENTION

Various plasma jet devices, such as those which employ a direct current and an ionized gas, are useful for generating a plasma jet for spectrometric analysis or for studies of high-temperature chemical and physical phenomena of various materials. In particular, such plasma jet devices are often employed in a spectrometer system, such as in an echelle spectrometer of the type described in U.S. Pat. No. 3,658,423, wherein a prism and echelle grating are employed and so mounted to provide rotation in two directions, thereby providing adjustment of the vertical and horizontal components of the dispersed energy in the exit focal plane of the spectrometer. Of course, plasma jet devices may be employed usefully in other spectrometers and in other apparatus where high-temperature excitation of a sample material is desired.

One plasma jet or excitation source useful, for example, in spectroscopic analysis, is described in U.S. Pat. No. 3,596,128. Such a plasma jet device includes a swirl chamber surrounding an anode electrode, into which swirl chamber a premixed atomized sample to be observed and an ionizing carrier gas are introduced. An anode is disposed in the chamber and located opposite an orifice. A cathode is located externally to and spaced from said chamber and at an angle to the axis of the plasma column, so that the cathode is offset from said plasma column. The plasma flame, after exiting from the swirl chamber through the orifices, is bent at an angle to the axis of the plasma column to contact said cathode electrode. This plasma device, while representing an improvement over the prior art, presents certain difficulties associated with the construction of the device.

An improvement of this plasma jet device is described in U.S. Pat. No. 4,009,413, and is hereby incorporated by reference in its entirety. The improved plasma jet device comprises an anode electrode and a cathode electrode, with each of the electrodes spaced apart and positioned such that their axes, if extended, would intersect at an angle. Each of the electrodes contains a coaxial sleeve element surrounding the electrodes through which flows an ionizable gas. The ionizable gas in operation forms the plasma jet and provides a continuous column of ionized gas between the anode and cathode electrodes, the plasma jet being characterized in such form by an inverted V-form shape. The plasma jet presents a reaction or excitation zone within the plasma jet at the lower region of the intersection of the extended axis of the anode and cathode electrodes. The plasma jet also includes an external means to introduce a sample, typically in aerosol form, and particularly in an ionizable carrier gas, upwardly between the anode and cathode, so that the sample is introduced directly into the reaction or excitation zone of the plasma arc.

In these prior-art plasma arc devices, certain difficulties in operation of the devices have been found in that the position of the plasma arc tends to move about, and, therefore, the excitation or reaction zone moves in position. With such movement of the excitation zone, there is a variation and difference in intensity of the spectrum from the sample being introduced into the zone, and, a difference in the quality and quantity of the spectrometric data. The spectrometric data obtained changes with such destabilization of the plasma arc position.

In addition, the prior-art devices have required employment of tungsten anodes. The use of a tungsten anode, rather than, for example, a graphite anode in combination with a tungsten cathode, creates certain difficulties in that the spectral level of tungsten is very high, and provides for a substantial number of up to 4,000 interfering tungsten lines in the spectrum, which may cause interference sometimes with the analysis of the spectrometric data obtained. In contrast, the employment of the graphite anode provides only a few interfering lines in the spectrum.

SUMMARY OF THE INVENTION

The invention concerns an improved plasma jet device, a method of operating the device and using such device and relates to a plasma jet device characterized by an inverted Y-type ionizing gas discharge plasma jet and the employment of a plurality of electrodes of one polarity with a lesser number of electrodes of the opposite polarity. More particularly, the invention is directed to an improved plasma jet device and method of operation, wherein the plasma jet is stabilized in position with the employment of a combination of two anode electrodes positioned such that their axes, if extended, would intersect at an angle and a third cathode electrode spaced apart from the offset from the plane of said anode electrodes. The plasma jet so formed is bent at an angle to the axis of the plasma column to provide for the formation of a stabilized plasma arc, and which device permits the employment of graphite as the anode electrodes.

It has been discovered that a plasma jet device, having a reaction or excitation zone which is stabilized in position, is obtained through the employment of first and second electrodes of one polarity in combination with a third electrode of a different and opposite polarity than the first and second electrodes, and with the first and second electrodes spaced apart in a position such that their axes, if extended, would intersect at an angle; for example, an angle of 60 to 90 degrees and preferably about 75 degrees, while the third electrode is spaced apart from the angle of intersection of the first and second electrodes and is offset from the plane formed by the intersecting axes, and typically and preferably is offset substantially at a right angle from the plane so as to form in operation a plasma jet of a column of ionized gas between the electrodes, with the plasma jet being characterized by an inverted Y-form. The excitation or reaction zone in the Y-shaped plasma jet is formed at the lower region of the intersection of the extended axes of said first and second electrodes. The plasma jet so formed has an excitation or reaction zone of stabilized position so that the plasma jet device, when employed, for example, in an emission spectroscopy, provides for a constancy in intensity of the spectrum and a reduced tendency of the drifting of the spectrometric data due to destabilization of the zone.

The plasma jet device includes coaxial sleeve means to surround the electrodes with an ionizable gas to form the inverted Y-shaped column of ionized gas. In operation, typically the gas is argon or a similar ionizable gas employed in plasma jet devices. The plasma jet device also includes a stable DC power-supply means, and preferably comprises two separate power supplies with the single electrode of one polarity being in common electrical communication with each of the power supplies and with each power supply separately communicating with one of the other electrodes of the other polarity. Preferably, the plurality of electrodes are the anode electrodes and the single or other electrode is a cathode electrode. The cathode electrode is typically a tungsten electrode, while the anode electrodes may be composed of graphite or tungsten.

It has been found that the inverted Y plasma jet of the improved plasma jet of the invention is very stable in position. It has been found that, in an inverted V-type plasma jet discharge, such as that described in U.S. Pat. No. 4,009,413, there is a magnetic field with a very high field strength which surrounds the plasma jet, particularly where the ionized gas meets at the intersection. In addition, it has been found that, due to the different polarities, there is a tendency for the column of ionized gas or the plasma to be pushed apart at the excitation of reaction zone formed by the intersection of the ionized columns of gas. Thus, this different polarity of the ionized gas columns, as they come together in the inverted V with the magnetic field, tends to push the gas columns apart and to destabilize or move about the reaction or excitation zone.

Furthermore, where the plasma jet device is employed with a means of introducing an aerosol sample material to the reaction zone, such as shown and described in U.S. Pat. No. 4,009,413, the operation of such an aerosol nebulizer further tends to push the plasma columns apart and to destabilize the plasma jet position. Thus, use of an aerosol sample introduction means, particularly where the same is introduced beneath the reaction zone in an ionized gas stream and at a relatively high gas velocity, coupled with the different polarities of the gas stream in the magnetic field, causes destabilization of the plasma jet, so that spectrometric data obtained is not constant in quality or intensity.

It has been discovered that the employment of a third cathode electrode offset from the plane of the intersecting axis of the plasma jet provides a stabilized position plasma arc. The electrode combination as described stabilizes the plasma arc, since the two electrodes legs of the inverted Y are of the same polarity, and the ionized column of gas emitted from the first and second electrodes move together in the same direction and are not pushed apart, so that the plasma jet can come together in a defined stable reaction or excitation zone. This results in better position stability, so that, even though an aerosol means is employed to direct a sample material and ionized carrier gas directly into the reaction zone, the reaction zone is not destabilized as in prior-art plasma devices.

In addition, it has been found that an important design feature of the three-electrode plasma art device is that the device permits the use of graphite as the anode in place of tungsten for the anode, although tungsten may be used if desired. The use of graphite is very desirous as an anode, since the graphite provides only a few carbon lines in the spectrum.

It also has been discovered that the third or cathode electrode should not be positioned directly above the inverted V formed by the first and second electrodes, but should be offset from the plane formed by the intersecting axes of the first and second electrodes, and typically positioned so that there occurs a bending of the plasma jet, and preferably, a bending of the plasma arc in a general perpendicular direction from the plane of the intersecting axes. It has been found that, if the third electrode is directly aligned in the axes plane, there are problems of contamination, while, with an offset position and a bending of the plasma jet, good stabilization without contamination is obtained.

A variety of DC power sources may be employed as the power source for the jet device; however, in the preferred embodiment, two power sources are employed as a power supply with a common cathode. The power supplies are common with the cathode electrode with respect to the cathode secured to the respective power supply. Typically, the cathode electrode remains as a tungsten or metal electrode, since it carries a very high amperage.

The invention will be described in connection with its preferred embodiments; however, it is recognized that various changes and modifications may be made to the embodiment as described by those people skilled in the art, without departing from the spirit and scope of the invention.

BRIEF DESCRIPTION OF THE DRAWING

The drawing shows a schematic representative view of a plasma jet device.

DESCRIPTION OF THE EMBODIMENTS

Figure 1:
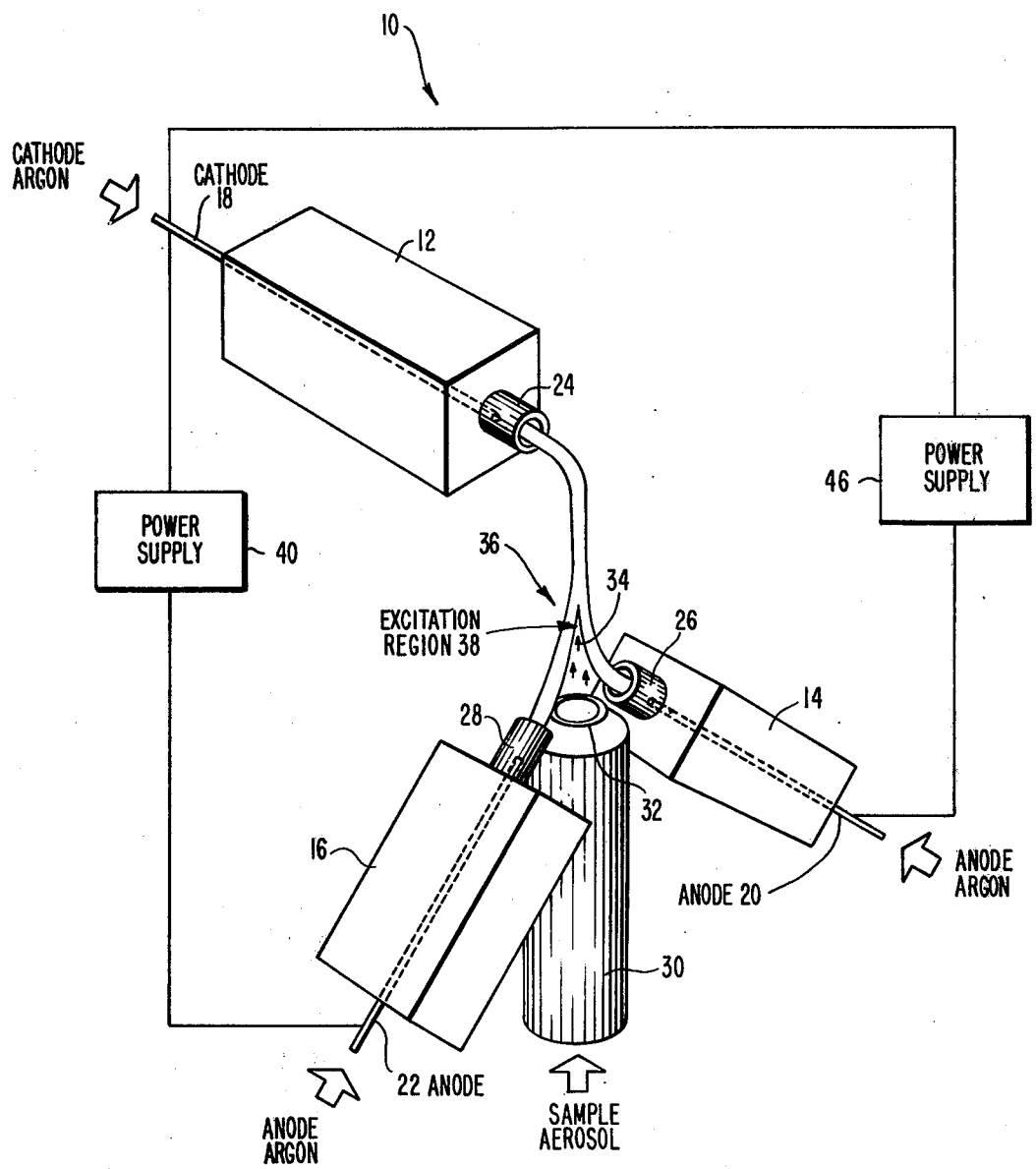

The plasma jet device 10 comprises support block means 12, 14 and 16 for the electrodes, and includes first and second anode electrodes 20 and 22 of graphite or tungsten which, if their axes are extended, intersect at an angle; for example, 75 degrees, and a third cathode electrode 18 of tungsten. The electrodes 18, 20 and 22 are positioned, respectively, in ceramic coaxial sleeve elements 24, 26 and 28 in the support means 12, 14 and 16. An ionizable gas such as argon is introduced into one end of each of the ceramic sleeve elements and flows about the electrodes in the respective sleeves to form in operation the plasma jet. There are means (not shown) to provide for the axial movement of the electrodes within the ceramic sleeves, so that the electrodes may be extended and withdrawn as desired and then secured in a desired fixed position in operation.

Directly below the intersecting axes of the electrodes 20 and 22 is a nebulizer or aerosol sample introduction means of comprising a nebulizer 30 having an outlet 32, whereby a sample material 34 is placed in aerosol form in a gas stream; for example, in an ionizable gas stream, and introduced through the outlet 32 directly into the excitation region 38 of the plasma jet formed. The plasma jet 36 as illustrated, is in the form of an inverted Y. The device includes two constant current DC power supplies, 40 and 46, common electrical leads going to the cathode electrode 18 and with leads from power supply 40 to the anode 22 and from power supply 46 to the anode 20. The arrows above the outlet 32 of the nebulizer 30 schematically illustrate the flow path of the sample material being introduced into the excitation region 38.

In operation, a laminar flow of an ionized gas is maintained around the electrodes 18, 20 and 22, while a sample material 34 is introduced as a laminar flow of an aerosol in an argon carrier through nebulizer 30 and the outlet 32 directly into the excitation zone 38 formed in the plasma jet 36. The plasma jet formed will follow the flow of the ionized gas from the sleeve elements 26 and 28 of the anodes 20 and 22, due to the magnetic attraction produced by current flowing in the same direction from each anode electrode. The excitation region, as illustrated, is between and just below the point where the two plasma columns of ionized argon from the anode electrodes combine at that point of intersection.

The ionized plasma jet is initiated by extending the cathode electrode 18 and the anode electrodes 20 and 22 outside of their respective ceramic sleeves, so that the cathode 18 and one anode electrode 20 or 22 come into contact, while the other anode electrode 20 or 22 is in close vicinity, but not in a touching relationship. As the cathode electrode 18 is withdrawn after contact, with the electrodes connected to a power supply as illustrated, and the argon gas flowing, a plasma jet is formed by the ionized argon gas, allowing the second anode also to be placed in a conducting relationship. Finally, the three electrodes are withdrawn as desired to their operating positions with their ends slightly inside the separate ceramic sleeve elements 24, 26 and 28.

What is claimed is:

1. A plasma jet device adapted for use in a spectrometer system, which plasma jet device comprises in combination:
   (a) a first and second electrode of one polarity;
   (b) an electrode of a different and opposite polarity than the first and second electrodes;
   (c) the first and second electrodes spaced apart and nonsymmetrically positioned such that their axes, if extended, would intersect at an acute angle;
   (d) the electrode of different polarity spaced apart from the angle of intersection of the first and second electrodes and offset from the plane formed by the intersecting axes;
   (e) means surrounding the electrodes to flow an ionizable gas about the said electrodes and to form in operation a plasma jet of a column of ionized gas between the said electrodes
   (f) an excitation zone formed by the ionized gas of the plasma jet between the acute angle of the first and second electrodes and at the lower region of the intersection of the extended axes of the first and second electrodes, the plasma jet containing the excitation zone characterized by an inverted Y-shape of the ionized gas; and
   (g) means to introduce a sample material to be analyzed spectrometrically directly into the lower region of the excitation zone and between the acute angle of the electrodes of the plasma jet, whereby a plasma jet, having an excitation zone of stabilized position, is maintained during operation of the device to provide for a constancy in intensity of the spectrum of the sample material.

2. The device of claim 1 which includes a power supply means and means to communicate electrically between the power supply means and each of the said electrodes.

3. The device of claim 2 wherein the power supply means comprises two separate constant current DC power supply means, each of the power supply means is in common electrical communication with the electrode of different polarity.

4. The device of claim 1 wherein the first and second electrodes are anode electrodes and the electrode of different polarity is a cathode electrode.

5. The device of claim 4 wherein the anode electrodes are graphite electrodes and the cathode electrode is a tungsten electrode.

6. The device of claim 1 wherein the means to introduce the material into the excitation zone comprises a means to introduce directly upwardly an aerosol sample of the sample material to be analyzed in an ionizable gas stream into the lower region of the excitation zone of the plasma jet between the first and second electrodes.

7. The device of claim 1 wherein the electrode of different polarity is positioned substantially perpendicular from the plane formed by the extended axes of the first and second electrodes.

8. The device of claim 1 wherein the first and second electrodes are anode electrodes composed of graphite and the third electrode is a cathode electrode, which electrodes are the only electrodes employed in the plasma jet device.

9. An emission spectrometer system which includes the plasma jet device of claim 1 as a source of excitation of the spectrometric sample material to be analyzed by the system.

10. The device of claim 9 wherein the spectrometer system comprises a prism and echelle grating so mounted as to provide for rotation in two directions to provide for adjustment of the vertical and horizontal components of the dispersed spectral energy in the exit focal plane of the spectrometer.

11. A plasma jet device adapted for use in a spectrometer system, which plasma jet device comprises in combination:
   (a) first and second graphite anode electrodes;
   (b) a cathode electrode;
   (c) the first and second electrodes spaced apart and nonsymmetrically positioned such that their axes, if extended, would intersect at an acute angle of about 60° to about 90°;
   (d) the cathode electrode of tungsten positioned substantially perpendicular and offset from the plane formed by the extended axes of the first and second electrodes;
   (e) coaxial sleeve means surrounding the electrodes to permit the flow of an ionizable gas about the said electrodes and to form in operation a plasma jet of a column of ionized gas between the said electrodes;
   (f) an excitation zone formed by the ionized gas of the plasma jet between the acute angle of the first and second electrodes and at the lower region of the intersection of the extended axes of the first and second electrodes, the plasma jet containing the excitation zone characterized by an inverted Y-shape of the ionized gas;
   (g) power supply means which comprises two separate DC power supply means, each of the power supply means in electrical communication with one of the anode electrodes with the cathode electrode; and
   (h) a means to introduce a sample material to be analyzed spectrometrically into the lower region of the excitation zone which comprises a means to introduce directly upwardly into the lower region of the excitation zone an aerosol sample of the material in an ionizable gas stream into the excitation zone of the plasma jet whereby a plasma jet having an excitation zone of stabilized position is maintained during operation of the device.

12. An emission spectrometer system which includes the plasma jet device of claim 11 as a source of excitation of the spectrometric sample material to be analyzed by the system.

13. A method for spectrometrically analyzing a sample material, which method comprises:

(a) positioning a spaced-apart first and second electrodes of the same polarity such that their axes, if extended, would intersect an an acute angle;

(b) positioning an electrode of different and opposite polarity than, and spaced apart from, the first and second electrodes and offset from the plane formed by the intersecting axes of the first and second electrodes;

(c) flowing an ionizable gas about the axes of said electrodes to form in operation a plasma jet formed of a continuous column of ionized gas between the said electrodes;

(d) forming said plasma jet having the shape of an inverted Y, the plasma jet having an arc-like-shaped excitation zone formed at the lower region of the intersecting axis, the excitation zone stabilized in position in the plasma jet;

(e) introducing a sample material to be spectrometrically analyzed directly into the lower region of the excitation zone between the said electrodes; and (f) spectrometrically analyzing the spectra obtained from the sample material in the stabilized excitation zone.

14. The method of claim 13 which includes positioning the third electrode offset and substantially perpendicular to the plane of the intersecting axes of the first and second electrodes.

15. The method of claim 13 wherein the third electrode is a cathode electrode and the first and second electrodes are anode electrodes.

16. The method of claim 15 wherein the cathode electrode is a tungsten electrode and the electrodes are either both tungsten or both graphite electrodes.

17. The method of claim 15 which includes supplying electrical DC current to the cathode and first anode electrode from one DC power supply and to the cathode and second anode electrode from another separate DC power supply.

18. The method of claim 13 which includes introducing a sample material in aerosol form in a stream of ionizable gas into the stabilized excitation zone of the plasma jet.

* * * * *